US009327303B2

(12) United States Patent
Wang et al.

(10) Patent No.: US 9,327,303 B2
(45) Date of Patent: May 3, 2016

(54) MICROFLUIDIC DROPLET GENERATOR

(75) Inventors: Wei Wang, Singapore (SG); Zhiping Wang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 78 days.

(21) Appl. No.: 13/980,273

(22) PCT Filed: Sep. 20, 2011

(86) PCT No.: PCT/SG2011/000323
§ 371 (c)(1),
(2), (4) Date: Sep. 26, 2013

(87) PCT Pub. No.: WO2012/099532
PCT Pub. Date: Jul. 26, 2012

(65) Prior Publication Data
US 2014/0017150 A1    Jan. 16, 2014

(30) Foreign Application Priority Data

Jan. 17, 2011    (SG) ................ 201100303-5

(51) Int. Cl.
| | |
|---|---|
| *B01L 3/00* | (2006.01) |
| *B05B 17/06* | (2006.01) |
| *B01L 3/02* | (2006.01) |
| *A61M 11/00* | (2006.01) |
| *A61M 15/00* | (2006.01) |
| *G01N 35/10* | (2006.01) |

(52) U.S. Cl.
CPC .......... *B05B 17/0615* (2013.01); *A61M 11/005* (2013.01); *B01L 3/0268* (2013.01); *A61M 15/0085* (2013.01); *B01L 2300/0816* (2013.01); *B01L 2300/123* (2013.01); *B01L 2400/0439* (2013.01); *B01L 2400/0478* (2013.01); *B01L 2400/0481* (2013.01); *G01N 2035/1041* (2013.01)

(58) Field of Classification Search
None
See application file for complete search history.

(56) References Cited

U.S. PATENT DOCUMENTS

| | | | |
|---|---|---|---|
| 5,510,816 A * | 4/1996 | Hosono et al. .................. 347/10 |
| 5,672,885 A * | 9/1997 | Allen et al. ................ 250/559.3 |
| 5,964,381 A * | 10/1999 | El-Hage et al. ............... 222/386 |
| 6,536,682 B1 | 3/2003 | Schnupp et al. |
| 2004/0021068 A1 * | 2/2004 | Staats ........................... 250/288 |
| 2008/0286751 A1 | 11/2008 | Renaud et al. |
| 2009/0218412 A1 * | 9/2009 | Wardle et al. ..................... 239/1 |
| 2011/0096122 A1 * | 4/2011 | Silverbrook .................... 347/44 |

OTHER PUBLICATIONS

"International Application Serial. No. PCT/SG2011/000323, International Preliminary Report on Patentability mailed Aug. 21, 2012", 10 pgs.
"International Application Serial No. PCT/SG2011/000323, International Search Report mailed Dec. 14, 2011", Nov. 23, 2014.
Ahamed, M. J., "A Piezoactuated Droplet-Dispensing Microfluidic Chip", *Journal of Microelectromechanical Systems*, 19(1), (Feb. 2005), 110-119.
Yamahata, C., "Plastic Micropump With Ferrofluidic Actuation", *Journal of Microelectromechanical Systems*, 14(1), (Feb. 2005), 96-102.

* cited by examiner

*Primary Examiner* — Jill Warden
*Assistant Examiner* — Timothy G Kingan
(74) *Attorney, Agent, or Firm* — Schwegman Lundberg & Woessner, P.A.

(57) ABSTRACT

A microfluidic droplet generator device, a kit of parts for assembling a microfluidic droplet generator device, and a method of generating microfluidic droplets. The generator device comprises a substrate; a microfluidic channel formed in the substrate; a fluid outlet in fluid communication with the microfluidic channel; and a mechanical element configured such that vibration of the mechanical element causes droplet dispensing from the fluid outlet.

17 Claims, 9 Drawing Sheets e)

MICROFLUIDIC DROPLET GENERATOR

PRIORITY CLAIM TO RELATED APPLICATIONS

This application is a U.S. National Stage application filed under 35 U.S.C. §371 of international application PCT/SG2011/000323, filed 20 Sep. 2011, and published as WO 2012/099532 A1 on 26 Jul. 2012, which claims priority under 35 U.S.C. 119 to Singapore Application No. 201100303-5, filed on Jan. 17, 2011, the contents of which applications and publication are incorporated herein by reference in their entirety.

FIELD

This disclosure relates broadly to a microfluidic droplet generator device, and to a kit of parts for assembling a microfluidic droplet generator device, and to a method for generating microfluidic droplets.

BACKGROUND

Both industry and research communities have the need for the controlled generation of liquid microdroplets with uniform characteristics. The contents of droplets can e.g. be molten organics, polymers and metals. The produced droplets can e.g. be converted to gelled polymer beads or solidified metal beads used for drug delivery, tissue engineering, compounding, coating and proportioning in pharmaceutical, biomedical, plastic and cosmetic industry. The two major requirements for droplet generation typically are high throughput and monodisperse in size distribution. Additional requirements for pharmaceutical and biomedical applications include contamination free, and thus a disposable part (for the part in contact with the flowing liquid) will be preferable.

Conventional microfluidic platforms, fabricated with Polydimethylsiloxane (PDMS), Poly(methyl methacrylate) (PMMA), glass or silicon for generating single or double emulsions, are disposable. However such platforms cannot run at high throughput, e.g. more than 1 milliliter per minute in terms of the flow rate of disperse phase.

In the case where oil is used as the carrier phase and surfactants are employed to stabilize the droplet formation process and to avoid the coalescence of droplets, additional separation processes are required to retrieve crosslinked droplets or beads from the oil followed by a thorough washing to remove the surfactants adsorbed on the gelled droplets. Such separation processes typically involve surfactants, which is not preferred for many applications, e.g. for cells or bio-molecules encapsulation process.

Additionally, the need of several pressure controlled or syringe pumps for multiphase emulsion forming on chip also can make the scale-up very costly. Thus, in industry, conventional microfluidic platforms are currently not preferred, instead high-throughput methods, such as ink jet printing, piezo tubing ejection, vibration of chamber, are employed for the droplet formation. In droplet generators such as ink jet printing, piezo tubing ejection and vibration of chamber, the fluid contacts the print head, piezo vibrator or the vibration chamber. None of these parts are disposable since they are either expensive or cannot be easily separated from a complicated and integrated system. When change-over (change of dispensing liquid) is frequent, a thorough cleaning of liquid-contacting portions of the system is necessary. Such cleaning process is extremely tedious when the contamination control is strict, e.g. for the process of bio- or drug encapsulation.

There is therefore a need to provide a droplets/beads generation method and apparatus, that seek to address at least one of the above problem.

SUMMARY

In accordance with a first aspect of the present invention there is provided a microfluidic droplet generator device comprising a substrate; a microfluidic channel formed in the substrate; a fluid outlet in fluid communication with the microfluidic channel; a mechanical element configured such that vibration of the mechanical element causes droplet dispensing from the fluid outlet; and a medium member disposed to isolate the mechanical element from direct contact with a dispensing fluid.

The mechanical element may comprise a piston element coupled to the microfluidic channel.

The mechanical element may be formed integral with the substrate.

The device may further comprise a vibrational element coupled to the mechanical element for vibrating the mechanical element.

The device may further comprise a signal generator coupled to the vibrational element for controlling the vibrational element.

The device may further comprise a conduit element disposed on the substrate and in fluid communication with the microfluidic channel.

The conduit element may be configured for receiving the mechanical element.

The device may further comprise a positioning structure for receiving the mechanical element into the conduit element.

The conduit element may comprise a tube separate from the substrate or a capillary channel formed in the substrate.

The medium member may comprise a fluid medium

The fluid medium may comprise air, an inert gas, or an immiscible liquid.

The medium member may comprise a solid medium.

The solid medium may comprise a portion of the substrate.

The fluid outlet may comprise an outlet member coupled to the microfluidic channel.

The fluid outlet may be formed integral with the substrate.

The fluid outlet may be in the form of an opening hole on a surface of the substrate.

The fluid outlet may be formed on a protruding part of the substrate.

A wall thickness of the fluid outlet may have a controlled thickness for reduction of a fluid wetting area.

The fluid outlet at an exit for the fluid may have a smaller cross-section than any cross-section of the microfluidic channel.

In accordance with a second aspect of the present invention there is provided a kit of parts for assembling a microfluidic droplet generator device, the kit of parts comprising a substrate; a microfluidic channel formed in the substrate; a fluid outlet in fluid communication with the microfluidic channel; a mechanical element configured such that vibration of the mechanical element causes droplet dispensing from the fluid outlet; and a medium member disposed to isolate the mechanical element from direct contact with a dispensing fluid.

The kit of parts may further comprise a vibrational element coupled to the mechanical element for vibrating the mechanical element.

The kit of parts may further comprise a signal generator coupled to the vibrational element for controlling the vibrational element.

In accordance with a third aspect of the present invention there is provided a method of generating microfluidic droplets comprising providing a mechanical element in a microfluidic channel; and vibrating the mechanical element to control droplet dispensing from a fluid outlet in fluid communication with the microfluidic channel, wherein a medium member is disposed to isolate the mechanical element from direct contact with a dispensing fluid.

DESCRIPTION

When a laminar liquid jet is sprayed out from a small orifice, the capillary instability will cause the jet to breakup into droplet streams. Lord Rayleigh developed a linear stability analysis of the breakup of laminar Newtonian liquid jets in air, showing that the surface waves grow exponentially in time dependent on the liquid density, initial jet diameter, surface tension. In example embodiments by introducing forced resonant disturbance on the liquid jet, there is the possibility to obtain more uniform droplet stream.

The described embodiments provide a droplet generation technique developed by using a transmission media for disturbance to a fluid stream. The technique can preferably provide a non-contact, high-throughput, contamination-free microbeads production method based on disposable microfluidic platform in example embodiments.

Figure 1:
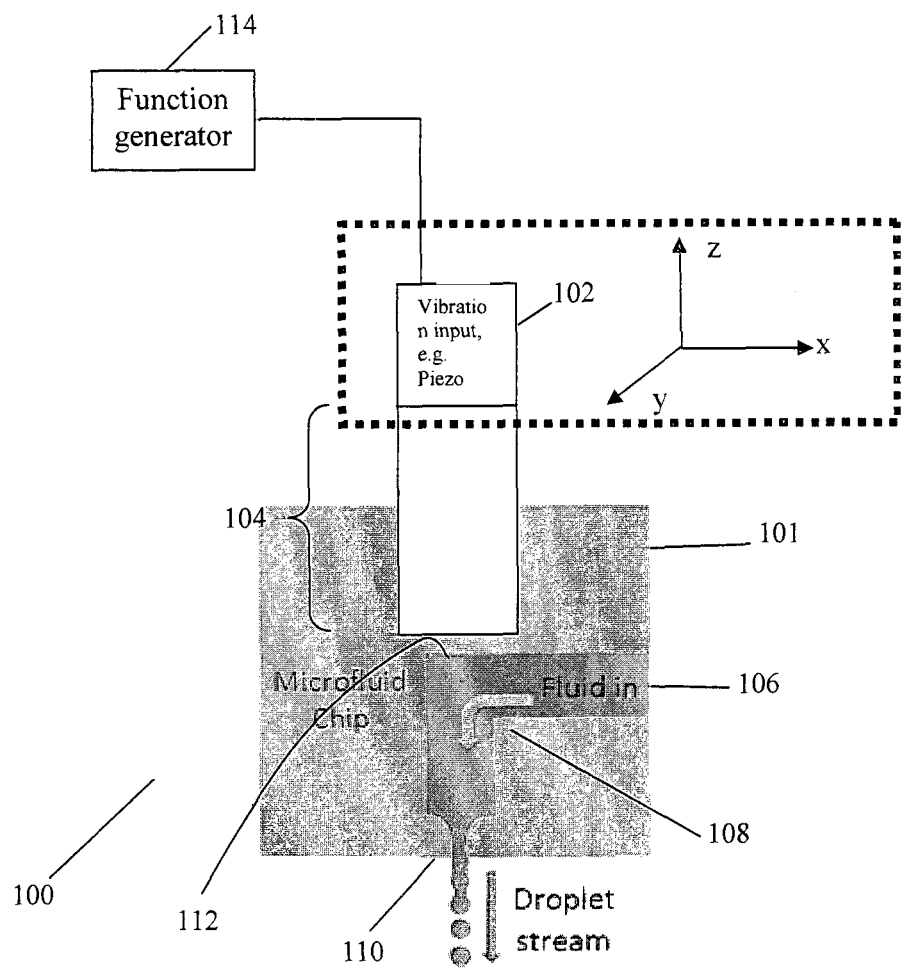
FIG. 1 is a schematic drawing showing a droplet generator device according to an example embodiment.

With reference to FIG. 1, the droplet generator 100 according to an example embodiment comprises a microfluidic chip 101, a vibration input element, here in the form of, but not limited to, a peizo element 102 and a coupling 104 between the microfluidic chip 101 and the piezo element 102. The microfluidic chip 101 comprises a fluid inlet 106, a channel 108 and a microfluidic outlet 110. The microfluidic channel 108 is bent between the inlet 106 and the outlet 110, with the vibration input element configured to deliver excitation at the bend 112. A function generator 114 is provided to drive the piezo element 102. The coupling 104 can have different forms in different embodiments, for example as shown in FIGS. 2a-e.

Figure 2:
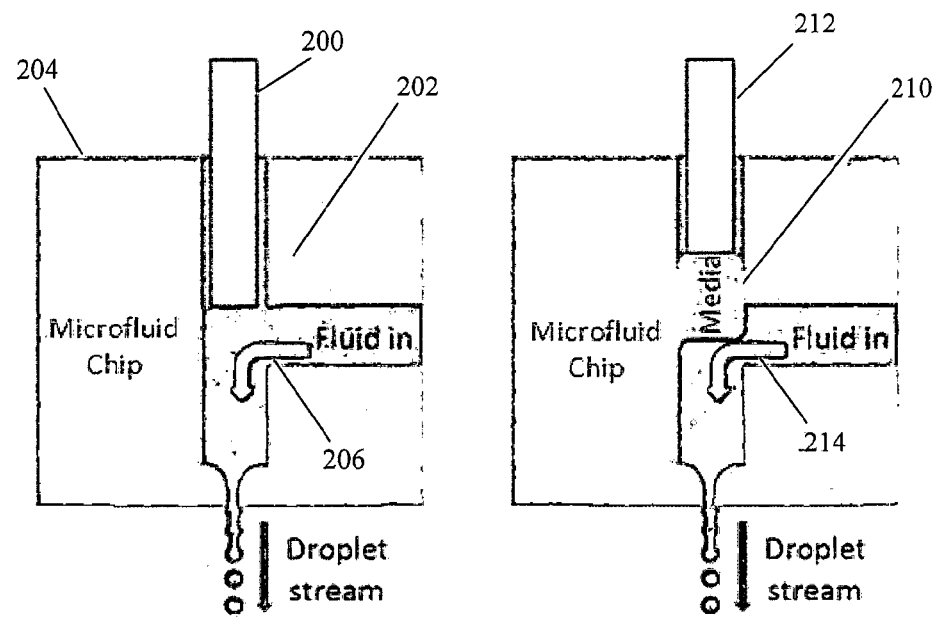
FIGS. 2a-e are schematic drawings show different implementations for a droplet generator device in different embodiments using different couplings.
Figure 2:
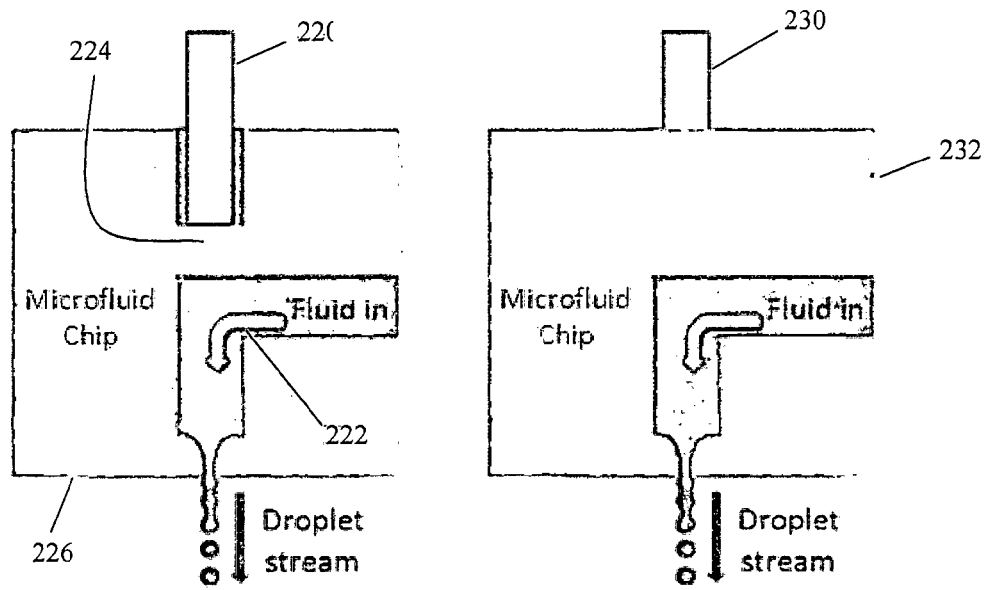
Figure 2:
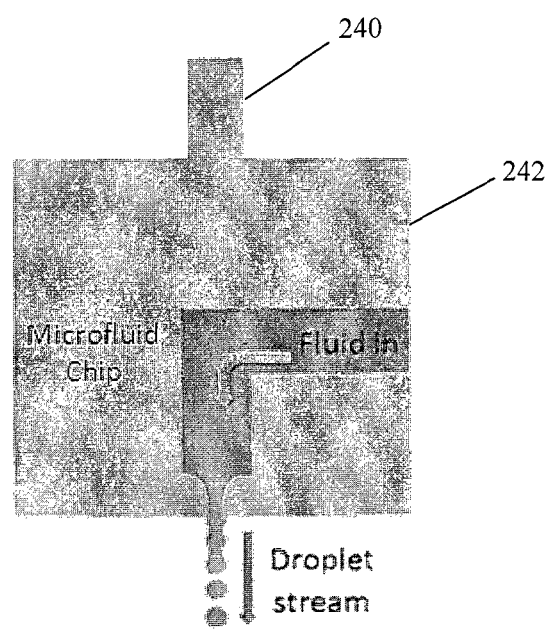

In FIG. 2a, a piston 200 is inserted into the microchannel 202 on chip 204, and directly contacts with the fluid 206 in the mircochannel 202. Through such direct contact, vibration of the piston 200 driven by the vibration input element (not shown) is transferred to the fluid 206 in the microchannel 202.

In FIG. 2b, there is a vibration transmission media 210 in between the piston 212 and the fluid 214. Through the media 210, for example, but not limited to an air bubble, vibration is transferred from piston 212 to the fluid 214.

In FIG. 2c, the piston 220 is isolated from the fluid 222 by a portion 224 of the chip 226 substrate.

In FIG. 2d, the piston 230 is not disposed into the chip 232. The piston 230 contacts the chip 232 loosely or is attached to the chip 232 by a rigid link such as, but not limited to, a screw, gluing etc.

In FIG. 2e, there is a protruding part 240 of the chip 242 substrate for the coupling of the chip 242 to the vibrating input element (not shown).

In the embodiments shown in FIGS. 2a-d, the piston may be formed as a separate part from the vibration input element, or the vibration input element may function as or may be formed integrally with a piston.

As illustrated in the example embodiments described above, in embodiments of the present invention periodic excitation by the vibration input element may be transmitted to the fluid through direct contact of either the vibration input element functioning as or formed integrally with a piston, or a separate piston driven by the vibration element with the fluid, or through a fluid medium such as, but not limited to, an air bubble or a solid medium such as, but not limited to, a polymeric material forming the microfluidic chip.

The fluid outlet in example embodiments has a narrowest orifice at the exit of the fluid. The fluid outlet can be fabricated separately and attached to the channel. Or the fluid outlet can be built directly on the microfluidic chip substrate. The fluid outlet of the microfluidic chip can have different forms in different embodiments, for example as shown in FIGS. 3a-d.

Figure 3:
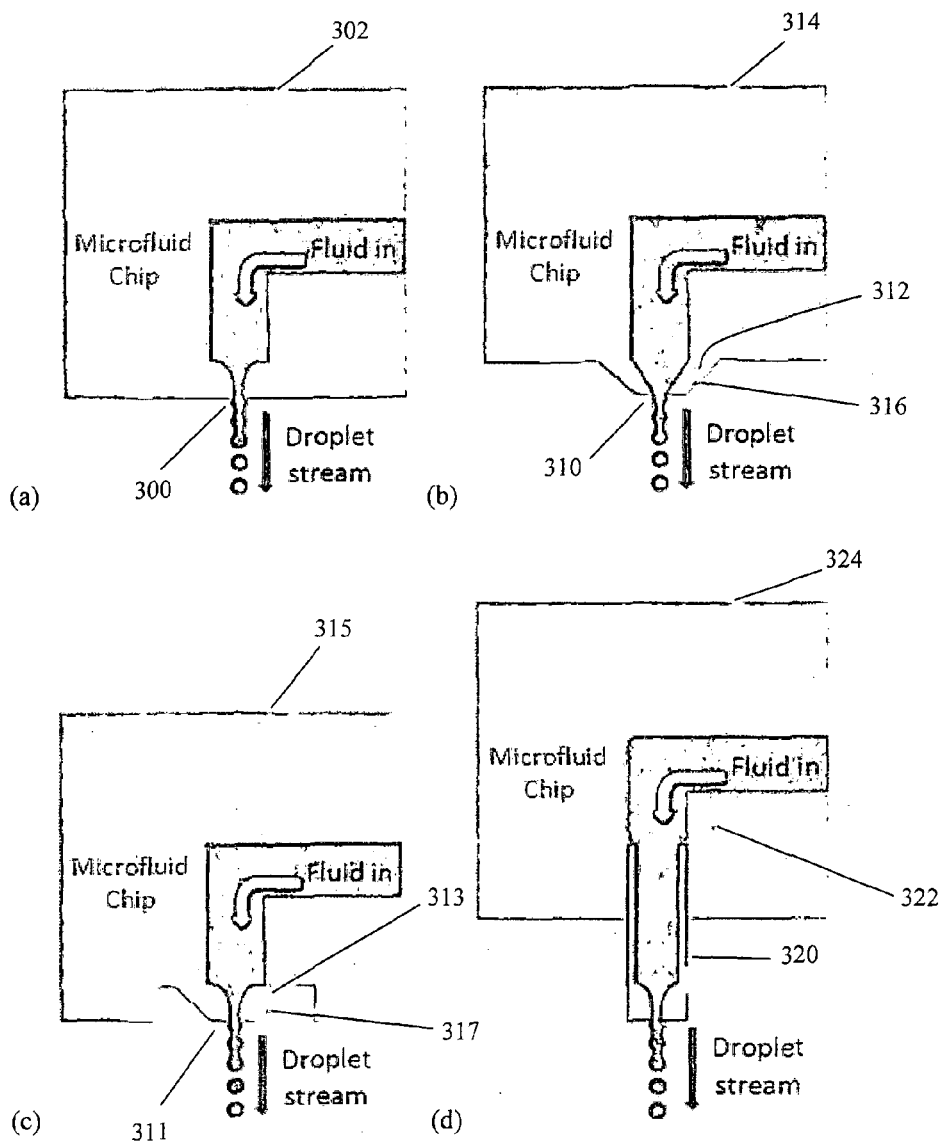
FIGS. 3a-d are schematic drawings show different implementations for a droplet generator device in different embodiments using different fluid outlets.

In FIG. 3a, the fluid outlet is in the form of an opening hole 300 on one of the flat surfaces of the chip 302 substrate.

In FIGS. 3b and c, the fluid outlet is in the form of an opening hole 310, 311 formed in a protruding part 312, 313 of the chip 314, 315 substrate. The channel wall 316, 317 of the protruding part 312, 313 is preferably controlled and minimized for the reduction of a fluid wetting area.

In FIG. 3d, the fluid outlet is in the form of a separately formed part 320 and disposed into the channel 322 of the chip 324 substrate. The part 320 can be made from materials such as, but not limited to, polymer, glass, steel, and ceramic. The polymer materials can be, but is not limited to, polycarbonate (PC), PMMA, etc, and can be formed through e.g. an injection molding process.

The fluid outlets in the example embodiments described above advantageously all have a narrowest orifice at the exit of fluid.

Figure 4:
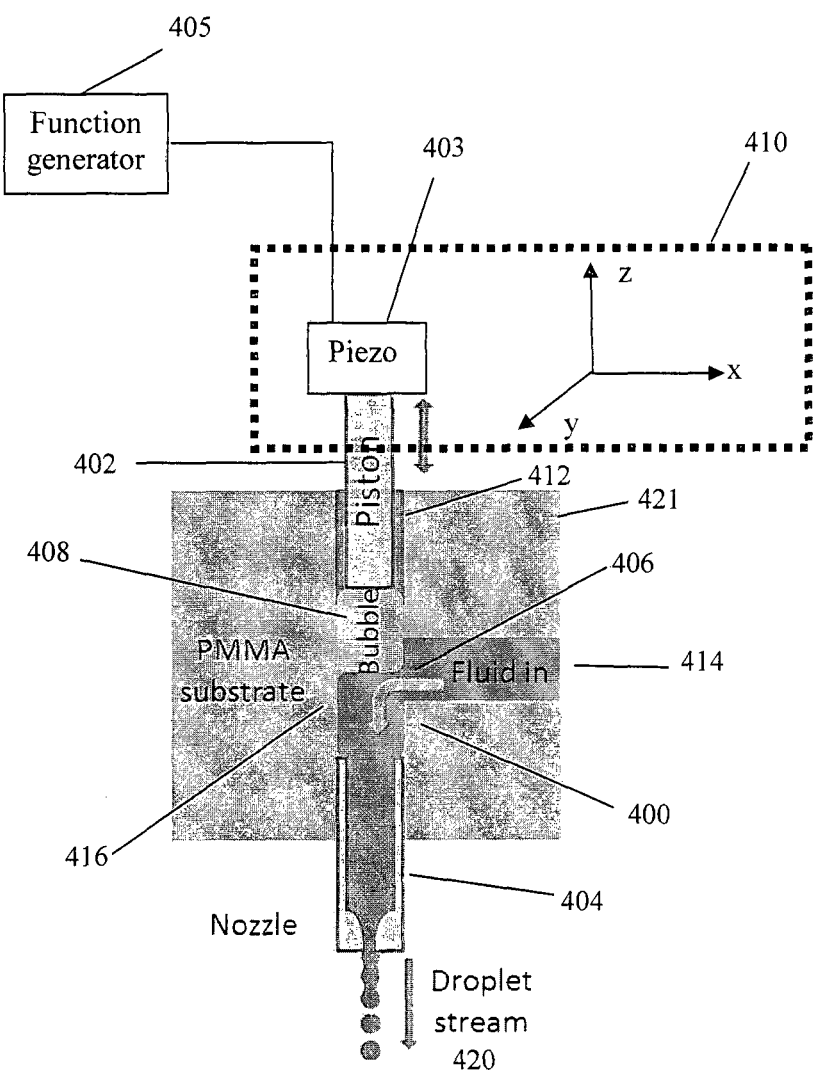
FIG. 4 is a schematic drawing showing a droplet generator device according to an example embodiment.

With reference to FIG. 4, the droplet generator, in one embodiment, comprises a microfluidic channel 400, a piston 402 driven by a vibrating element for example in the form of piezo or magnetic disc 403, a waveform generator to drive the vibrating element (such as a function generator 405) and a fluid outlet 404 to facilitate droplet formation, e.g. in the form of a glass capillary based fluid outlet. In the example embodiment, a disturbance is applied to a fluid stream 406 in the microchannel 400 by the vibrating piston 402 inserted in the microchannel 400. Besides direct contact between the piston 402 and fluid stream 406 in one embodiment, air, an inert gas or an immiscible liquid can be used as isolation between the piston 402 and the fluid stream 406 in different embodiments. The piston 402, e.g. in the form of a metal pin is attached to the piezo disc or magnetic 403 which is driven by the function generator. The piston 402 is inserted in a T-shape microchannel 400 in this embodiment to pass disturbance to the fluid stream 406 through an air bubble 408 enclosed in the channel 400 to implement controllable formation of essentially uniform droplets.

As shown in FIG. 4, the piezo driven piston 402 have a metal pin is attached to a 3-dimensional positioning system 410. With the 3-D positioning system such as a 3-D stage 410, the piston 402 is aligned and inserted into a glass capillary 412 (embedded in the channel 400) which forms the top part of the T-channel 400. The diameter of the piston 402 is matched with the inner diameter of the glass capillary 412 (about 450 μm in one example). Thus a high flow resistance is created for the top part of the T-channel 400 to prevent the flow-through of liquid. When liquid 406 is introduced into the T-channel 400 from the liquid inlet 414, it will thus flow towards the fluid outlet of the microfluidic chip 404 due to the flow resistance difference between the top and bottom parts of the T-channel 400. With piston 402 slightly away from the T-junction 416, the air bubble 408 will be trapped in between the piston 402 and the liquid 406 at the T-junction 416 and serve as a separation of the piston 402 and liquid stream 406. At such high flow rates, e.g. at about 4 ml/min, liquid 406 was ejected out of the fluid outlet 404 and formed a droplet stream 420 as shown in FIG. 4.

The metal piston 402 attached to the piezo disc 403 is loosely attached to the microfluidic device/substrate 421, which is disposable. Thus the actuator together with piston 402 is reusable. By making the diameter of piston 402 well matched with the inner diameter of the glass capillary 412, a high flow resistance is preferably created to prevent the flow towards the piston 402. Such design advantageously helps to trap e.g. the air bubble 408 in the T-channel 400 to avoid direct contact of piston 402 with liquid 406. By making the diameter of the piston 402 well matched with the inner diameter of the glass capillary 412, the movement of the piston 402 is also constrained in the longitudinal direction of the glass capillary 412. This makes the setup of the device simple with less concern on the misalignment of the piston 402 and capillary 412. The T-channel microfluidic device/substrate which has contact with the fluid 406 is disposable and simply built from polymer slides (i.e. PMMA, 40 mm×40 mm×4 mm in terms of width, length and thickness) and glass capillaries in this example embodiment. With a preferably light metal piston 402 instead of e.g. a fluid chamber attached to the vibrating element, the driving power needed is low. Thus for example a piezo disc driven by a function generator without power amplifier can preferably be used.

Figure 5:
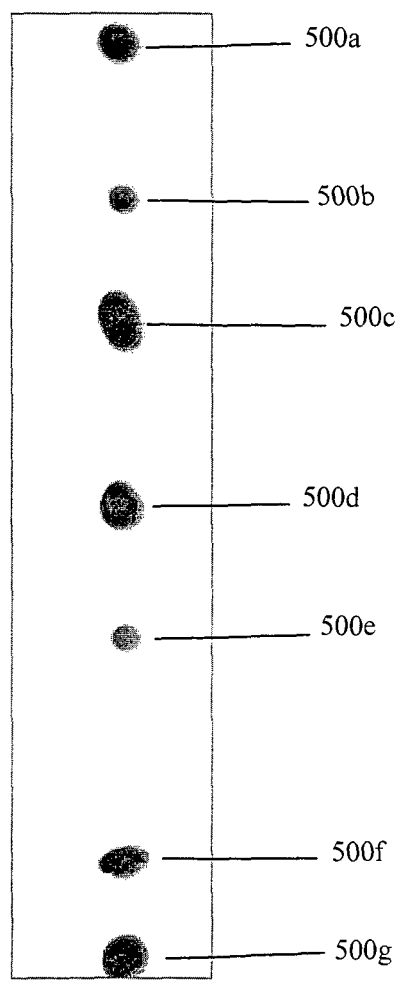
FIG. 5 shows an example image, extracted from a video captured by a high speed camera showing droplet generation by the device of FIG. 4 without activation of the piston.

FIG. 5 is an example image, extracted from a video captured by a high speed camera (50,000 frames per second), showing the droplets 500*a-g* formed and flying in the air, without turning on the function generator (a 33220A function generator, Agilent, in one example embodiment) to drive the piston 404 (FIG. 4). The droplet size is non-uniform and droplet intervals (droplet to droplet distance) are not consistent. At the same flow rate and set-up, by applying a square waveform (about 1470 Hz, Vpp about 10 Volts) to drive the piston 404 (FIG. 4), a much more stable droplet 600*a-f* stream is obtained as shown in the FIG. 6*a*. The droplet size is advantageously uniform and the droplet interval (droplet to droplet distance) is consistent. In other words, the fluid in the channel breaks up into a single file of substantially uniform droplets 600*a-f* upon exiting from the fluid outlet.

Figure 6:
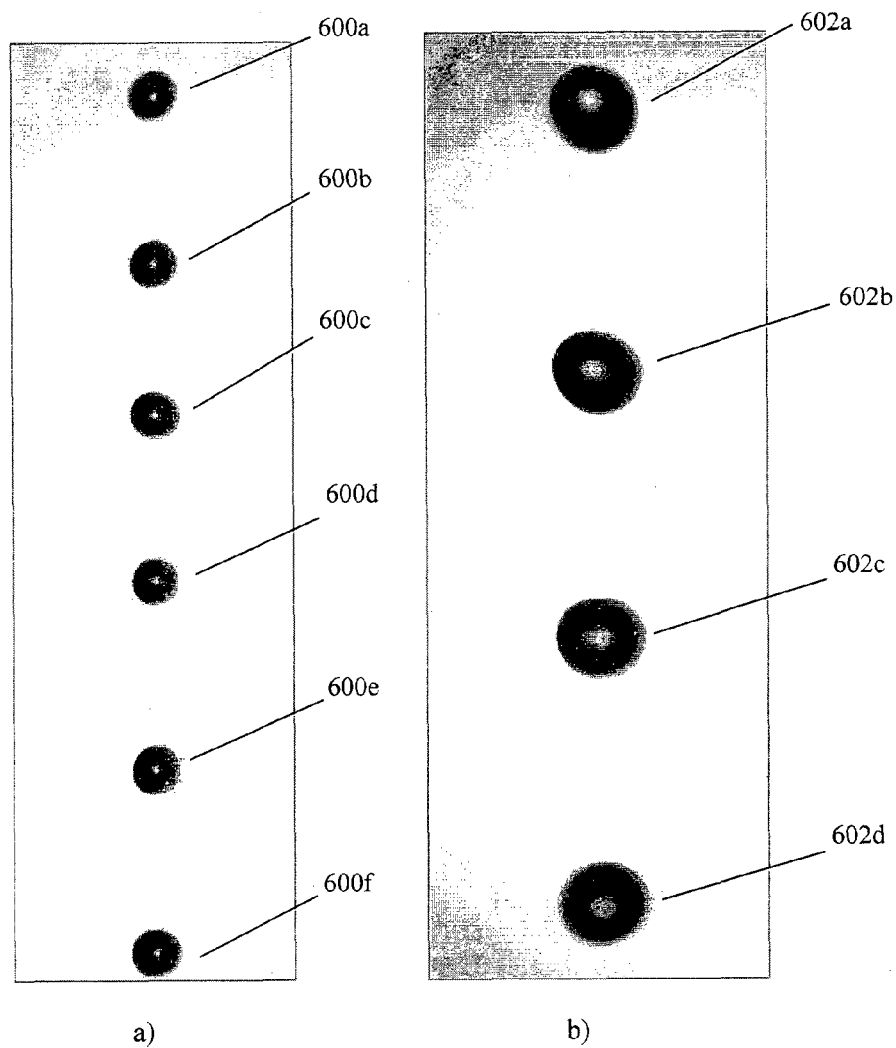
FIGS. 6a and b show respective example image, extracted from a video captured by a high speed camera showing droplet generation by the device of FIG. 4 with activation of the piston at different actuating signals.

Droplets of different dimensions can preferably be obtained by adjusting the diameter of the fluid outlet, flow rate as well as vibration frequency. Video captured by a high speed camera indicated that an optimized setup, the droplet generation rate is substantially the same as the vibration frequency. The droplet diameter can then be calculated or predicted by dividing the flow rate by the droplet generating frequency and this was formed to well match with droplet dimensions obtained from the video. As shown in FIG. 6*b*, large size droplets 602*a-d* (about 480 μm) were obtained in one embodiment with a flow rate of about 4 ml/min and a piezo frequency of about 1090 Hz.

Figure 7:
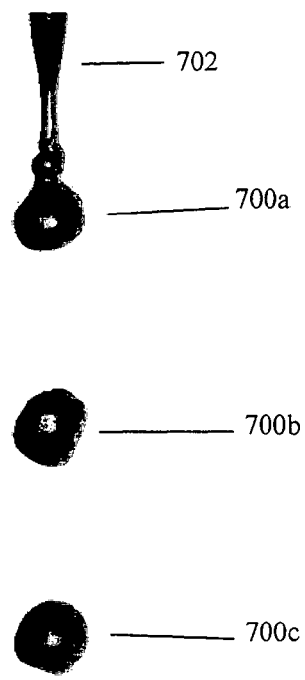
FIG. 7 shows an example image of the captured droplet stream at the fluid outlet of the device of FIG. 4 with activation of the piston.
Figure 8:
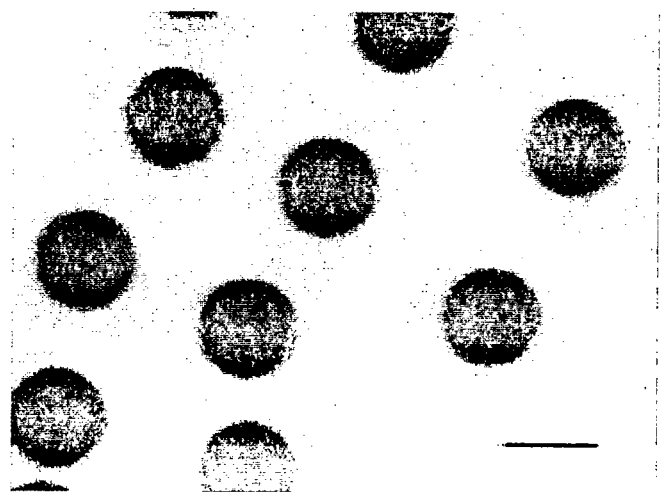
FIG. 8 shows an example image of part of a petri dish filled with oil as surfactant to for observation of size distribution of droplets generated according to an example embodiment.

An example image of the captured droplet stream at the fluid outlet of the chip according to an embodiment is shown in FIG. 7. The droplets 700*a-c* break up from the stream 702 consistently and in a stable manner under the applied disturbance. In other words, substantially uniform droplets 700*a-c* begin to take shape after exiting from the fluid outlet. The droplets can be collected to a petri dish filled with oil (e.g. oil containing 2 vol % span 80 (sorbitan monooleate) as surfactant for aqueous droplets to prevent droplet coalescence for droplets collected in the petri dish) for a better observation of their size distribution as shown in the example image in FIG. 8.

The disturbance generated at the bubble (408, FIG. 4) to liquid interface was also captured by the high speed camera. Analysis of the video data confirmed that the vibration of the bubble-liquid interface has substantially the same frequency as the vibration frequency of the actuator, e.g. the piezo disc. Once the vibration was cut off, there is no more vibration of the bubble-liquid interface observed. Thus the vibration of the air bubble (408, FIG. 4) did follow the vibration introduced by the actuator. This clearly indicates the role of the enclosed air bubble (408, FIG. 4) as a vibration transmission media in between the piston (402, FIG. 4) and fluid (406, FIG. 4).

The PMMA substrate, glass capillaries, metal pin and piezo disc are used in one example embodiment, all non-expensive items and could be considered as disposable items when there is a critical requirement on contamination control. In another embodiment, the metal pin could be made detachable from the piezo disc so that the piezo disc can be reused. With the microfluidic platform being simple, low cost and disposable in example embodiments, the market requirement for a monodisperse, contamination free and high throughput droplet generation process can advantageously be met.

The channel design in example embodiments is not limited to T-shape and can be Y-shape, irregular shape etc. and can have multiple "arms" instead of three. The fluid outlet can be of any other types of outlets, such as, but not limited to, polymer, steel, ceramic. As shown in the FIGS. 3*a-c*, instead of being attached to the channel, the fluid outlet can be built directly on the microfluidic device substrate. The channel for guiding the piston can be replaced by any other types of tubing and/or can be replaced by a built-in channel on the device/substrate, or may be omitted as shown in FIGS. 2*e, d*. The driving of the piston can be implemented using any types of vibrating elements, such as, but not limited to, piezo disc, magnetic vibrator, shaker or pneumatic actuator.

The microfluidic device/substrate is not limited to a PMMA substrate and can be glass, silicon, PDMS, Polycarbonate (PC) or any other polymer substrate. The fabrication of the integrated microfluidic platform can be, but is not limited to, standard micro-electro-mechanical (MEMs) process, plastic machining, injection molding or any other polymer molding processes.

Embodiments of the disclosed droplet generator described herein can find applications in for example, but not limited to, polymer microbeads production and biomedical industry (drug/cell encapsulation, tissue engineering), compounding, coating, pharmaceutical, plastic and cosmetic industry.

Figure 9:
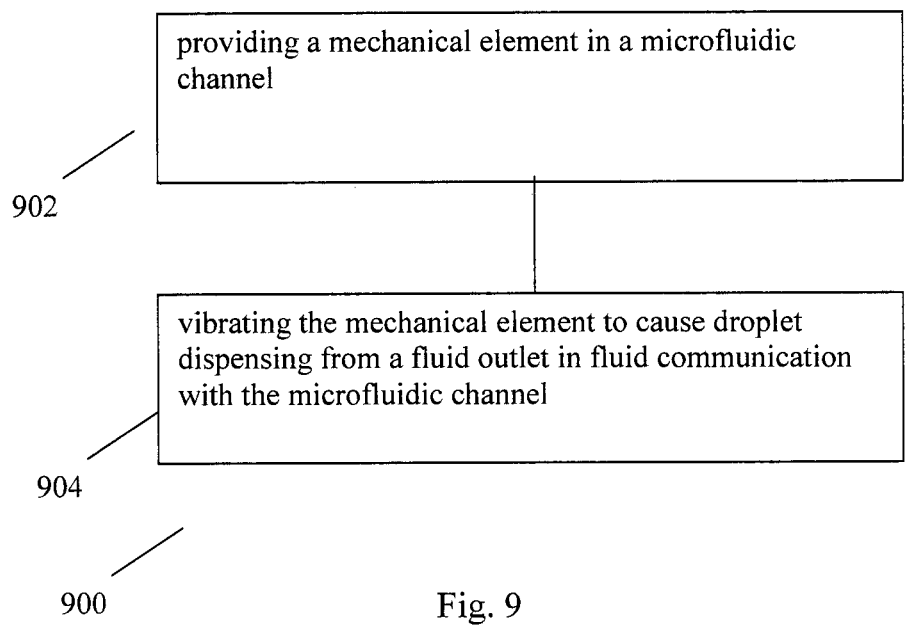
FIG. 9 shows a flow chart 900 illustrating a method of generating microfluidic droplets according to an example embodiment.

FIG. 9 shows a flow chart 900 illustrating a method of generating microfluid droplets according to an example embodiment. At step 902, a mechanical element is provided in a microfluidic channel. At step 904, the mechanical element is vibrated to cause droplet dispensing from a fluid outlet in fluid communication with the microfluidic channel.

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive.

The invention claimed is:

1. A microfluidic droplet generator device comprising:
   a substrate;
   a microfluidic channel formed in the substrate;
   a fluid outlet in fluid communication with the microfluidic channel;
   a mechanical element configured such that vibration of the mechanical element causes droplet dispensing from the fluid outlet; and
   a medium member disposed to isolate the mechanical element from direct contact with a dispensing fluid,
   wherein the medium member comprises a fluid medium;
   a vibrational element coupled to the mechanical element for vibrating the mechanical element; and
   wherein the mechanical element is associated with the microfluidic channel.

2. The device as claimed in claim 1, wherein the mechanical element comprises a piston element coupled to the microfluidic channel.

3. The device as claimed in claim 1, further comprising a signal generator coupled to the vibrational element for controlling the vibrational element.

4. The device as claimed in claim 1, further comprising a conduit element disposed on the substrate and in fluid communication with the microfluidic channel.

5. The device as claimed in claim 4, wherein the conduit element is configured for receiving the mechanical element.

6. The device as claimed in claim 5, further comprising a positioning structure for receiving the mechanical element into the conduit member.

7. The device as claimed in claim 4, wherein the conduit element comprises a tube separate from the substrate or a capillary channel formed in the substrate.

8. The device as claimed in claim 1, wherein the fluid medium comprises air, an inert gas, or a liquid immiscible with the dispensing fluid.

9. The device as claimed in claim 1, wherein the fluid outlet comprises an outlet member coupled to the microfluidic channel.

10. The device as claimed in claim 1, wherein the fluid outlet is formed integral with the substrate.

11. The device as claimed in claim 10, wherein the fluid outlet is in the form of an opening hole on a surface of the substrate.

12. The device as claimed in claim 10, wherein the fluid outlet is formed on a protruding part of the substrate.

13. The device as claimed in claim 12, wherein a wall thickness of the fluid outlet has a controlled thickness for reduction of a fluid wetting area.

14. The device as claimed in claim 1, wherein the fluid outlet at an exit for the fluid has a smaller cross-section than any cross-section of the microfluidic channel.

15. A kit of parts for assembling a microfluidic droplet generator device, the kit of parts comprising:
   a substrate;
   a microfluidic channel formed in the substrate;
   a fluid outlet in fluid communication with the microfluidic channel;
   a mechanical element configured such that vibration of the mechanical element causes droplet dispensing from the fluid outlet; and
   a medium member disposed to isolate the mechanical element from direct contact with a dispensing fluid,
   wherein the medium member is configured to comprise a fluid medium;
   a vibrational element configured to be coupled to the mechanical element for vibrating the mechanical element; and
   wherein the mechanical element is configured to communicate with the microfluidic channel.

16. The kit of parts as claimed in claim 15, further comprising a signal generator coupled to the vibrational element for controlling the vibrational element.

17. A method of generating microfluidic droplets comprising
   providing a microfluidic droplet generator device of claim 1;
   vibrating the mechanical element to cause droplet dispensing from a fluid outlet in fluid communication with the microfluidic channel,
   wherein a medium member is disposed to isolate the mechanical element from direct contact with a dispensing fluid, and
   wherein the medium member is configured to comprise a fluid medium.

* * * * *